United States Patent [19]

Farkas et al.

[11] Patent Number: 5,703,371
[45] Date of Patent: Dec. 30, 1997

[54] MODIFIED NOTCHED ENERGY FILTER NEUTRON RADIOGRAPHY CAMERA FOR NON-DESTRUCTIVE DETERMINATION OF HYDROGEN CONTENT OF IRRADIATED BWR FUEL ELEMENTS

[75] Inventors: David Michael Farkas, Benicia; Daniel Reese Lutz, San Jose, both of Calif.

[73] Assignee: General Electric Company, Schenectady, N.Y.

[21] Appl. No.: 689,565

[22] Filed: Aug. 12, 1996

[51] Int. Cl.⁶ .................. G01N 23/204; G01N 23/202
[52] U.S. Cl. .................. 250/390.02; 250/390.05; 250/473.1
[58] Field of Search .................. 250/390.02, 390.05, 250/473.1

[56] References Cited

U.S. PATENT DOCUMENTS

| | | | |
|---|---|---|---|
| 3,742,367 | 6/1973 | Grossman | 250/391 |
| 5,192,491 | 3/1993 | Schulz | 376/159 |

FOREIGN PATENT DOCUMENTS

| | | | |
|---|---|---|---|
| 1-18376 | 4/1989 | Japan | 250/390.02 |
| 1363038 | 12/1987 | U.S.S.R. | 250/390.02 |
| 1248916 | 10/1971 | United Kingdom | 250/390.02 |

OTHER PUBLICATIONS

A. Zeilinger and W. A. Pochman, "Neutron radiographic measurement of the diffusion of H in β–Ti, V, Nb and Ta" J. Phys. F: Metal Phys., vol. 7, No. 4, (1977) pp. 575–583, Apr. 19, 1977.

*Nuclear Technology*, "Detection of Parts–per–Million Levels of Hydrogen in Solids Using a Modified Notched Neutron Spectrum Technique," W. H. Miller, L. Lin, R. M. Brugger and W. Meyer, vol. 99, p. 252, 1992, (Aug.).

*Transactions of the American Nuclear Society*, "Determination of Zirconium Hydriding in Nuclear Fuel Pins Utilizing the Notched Neutron Spectrum Technique, " William H. Miller, David M. Farkas and Daniel R. Lutz, Jan. 12, 1996.

*Primary Examiner*—Constantine Hannaher
*Attorney, Agent, or Firm*—Nixon & Vanderhye P.C.

[57] ABSTRACT

A neutron radiography camera operates in cooperation with a neutron beam source for determining hydrogen content of irradiated BWR fuel elements. The camera implements the method using a notched neutron spectrum filter to determine the hydrogen content. The camera is specifically configured to take advantage of the tubular geometry of a nuclear fuel rod. Incident neutron beam ports are formed in a base unit that receives an incident filtered neutron beam. The ports aim the neutron beam at a periphery of the BWR fuel elements, which in the context of nuclear fuel rods includes zirconium alloy cladding. Collision of the neutrons with hydrogen in the cladding lowers their energy and scatters them at preferential angles. Scatter cavities defining scattered neutron paths are formed in the base unit, and absorber plates are disposed of terminal ends of the scatter cavities. The absorber plates become activated by resonance absorption from the neutrons scattered by hydrogen in the target fuel elements. The hydrogen content can be determined from the activated absorber plates.

21 Claims, 2 Drawing Sheets

MODIFIED NOTCHED ENERGY FILTER NEUTRON RADIOGRAPHY CAMERA FOR NON-DESTRUCTIVE DETERMINATION OF HYDROGEN CONTENT OF IRRADIATED BWR FUEL ELEMENTS

BACKGROUND

The present invention relates to nuclear reactor fuel assemblies and, in particular, to a radiography camera for determining the hydrogen content of irradiated BWR fuel elements.

In a typical boiling water nuclear reactor, a plurality of zirconium clad fuel rods are assembled in bundles and surrounded by a channel. The bundles and channel are immersed in a nuclear chamber filled with water. The fuel rods contain fuel that is burned to heat the water in the chamber, whereupon the steam exiting the chamber is used to generate power.

During operation, these zirconium clad fuel rods can be damaged by erosion, which generates a "perforation" in the fuel rod cladding. Similar "perforations" may result from slight defects in the fuel rod. The "perforation" can allow steam to egress inside the fuel rod, which breaks down to form hydrogen and oxygen. The oxygen reacts with the fuel, and the hydrogen typically forms hydrides with the zirconium metal. The hydrides embrittle the zirconium cladding causing secondary fuel rod failure. Hydrogen accumulation in the zirconium alloy cladding can also occur during normal reactor operation, but does not usually become a problem until extended burnups are reached.

It is advantageous to coordinate hydride levels with fuel rod mechanical properties as such is an important aspect of gauging fuel rod performance. Current methods of determining failed fuel rod hydrogen levels include a destructive technique (inert gas fusion, such as made by LECO), which has a minimum sensitivity of approximately 5 parts-per-million (ppm), and non-destructive conventional neutron radiography, which has a reliable minimum sensitivity of approximately 800 ppm. In the LECO analysis, the damaged rod is first removed from the core, the rod is sectioned into relatively small sections, and any remaining fuel in the fuel rod is removed. The section is placed in a high temperature flask and heated with a tin alloy. The section reacts and the hydrogen is driven off. A thermal conductivity measurement is made of the emitted gas to determine the cladding hydrogen level.

With this technique, however, the process is destructive, and subsequent tests with the same fuel rod section are impossible. With the non-destructive conventional neutron radiography technique, although the method is non-destructive, the sensitivity using this method is poor.

DISCLOSURE OF THE INVENTION

It is therefore an object of the invention to provide an apparatus that utilizes a non-destructive process for determining hydrogen content of irradiated BWR fuel elements. It is another object of the invention to provide a neutron radiography camera that utilizes a notched neutron spectrum filter for determining hydrogen content of the zirconium cladding an irradiated BWR fuel element.

These and other objects and advantages of the present invention are achieved by providing a neutron radiography camera operating in cooperation with a neutron beam source for determining hydrogen content of irradiated BWR fuel elements. The camera includes a base unit having a central elongated channel shaped to receive a BWR fuel element, an incident neutron beam port formed in the base unit that is tangentially aligned with the central elongated channel, a filter assembly disposed between the neutron beam source and the incident neutron beam port that selectively filters the neutron beam to remove certain energy levels, and an absorber plate disposed in a scattered neutron path. The filter assembly preferably includes a cadmium thermal neutron filter and an indium notched energy filter. A scatter cavity may be formed in the base unit along the scattered neutron path between predetermined angles from the central elongated channel relative to an incident angle of the neutron beam. In this regard, the absorber plate is disposed at a terminal end of the scatter cavity. Moreover, at least one forward scattered cavity is formed in the base unit along a forward scattered neutron path, wherein the forward scatter cavity is formed between predetermined obtuse angles from the central elongated channel relative to the incident angle of the neutron beam. Similarly, a back scatter cavity is formed in the base unit along a back scattered neutron path, wherein the back scatter cavity is formed between predetermined acute angles from the central elongated channel relative to the incident angle of the neutron beam. In this regard, at least two absorber plates are provided that are disposed at terminal ends of the forward scatter cavity and the back scatter cavity, respectively. The absorber plates preferably comprise indium foil.

The camera may include a support assembly rotatably disposed at opposite ends of the central elongated channel. The support assembly is adapted to rotatably support the BWR fuel element in the central elongated channel. The support assembly preferably includes a pair of bearing units secured to the base unit that facilitate rotation of the BWR fuel element. Furthermore, a motor may be provided connected to the support assembly that rotatably drives the support assembly about a central longitudinal access through the central elongated channel.

In accordance with another aspect of the invention, there is provided a neutron radiography camera for determining hydrogen content of irradiated BWR fuel elements. The camera includes a base unit having a central elongated channel shaped to receive a BWR fuel element, an incident neutron beam port formed in the base unit that is tangentially aligned with the central elongated channel and receives an incident filtered neutron beam, and a scatter cavity formed in the base unit that receives neutrons scattered from hydrogen in the BWR fuel element. The camera may further include a filter assembly disposed covering the incident neutron beam port that filters a neutron beam from a neutron beam source. The filter assembly preferably includes a cadmium thermal neutron filter and an indium notched energy filter. An absorber plate is preferably attached to the base unit at a terminal end of the scatter cavity. In this regard, the absorber plate is preferably formed of indium foil.

The camera may include a plurality of scatter cavities that are formed in the base unit between predetermined angles relative to an incident angle of the incident filtered neutron beam in accordance with a preferential path of scattered neutrons. The predetermined angles are preferably about 45° and 85°.

BRIEF DESCRIPTION OF THE DRAWINGS

These and other aspects of the invention will become apparent from the following detailed description when read in light of the accompanying drawings, in which.

BEST MODE FOR CARRYING OUT THE INVENTION

It has been determined that conventional non-destructive neutron radiography, which suffers from poor sensitivity, can be improved to more accurately detect hydrogen content in metals and hydriding and hydrogen embrittlement of zirconium. The modified neutron radiography technique employs a filtered neutron energy spectrum that heightens hydrogen detection sensitivity by the incident neutron beam being selectively filtered to remove certain energy levels.

In practice, a composite metal foil filter (made of cadmium to remove thermal neutrons and another material such as indium to remove certain energy windows) is employed to "notch" the energy spectrum of the neutron beam. The material to be tested (target) is placed in the filtered incident neutron beam. Collision (scattering events) of the neutrons with hydrogen in the target material lowers neutron energy and scatters the neutrons at preferential angles (when compared to other atoms in the target). An absorber plate of the same material as the energy filter (e.g., indium) placed in the preferential path of scattered neutrons will become activated by resonance absorption. The activated absorber plate is used to expose X-ray film as in conventional neutron radiography.

This process yields a quantitative measure of the hydrogen content of the target material. Hydrogen concentrations as low as 50 ppm in zircaloy coupons have been reported using this notched neutron spectrum technique. The technique has been described in several technical articles including, for example, an article entitled "Determination of Zirconium Hydriding in Nuclear Fuel Pins Utilizing the Notched Neutron Spectrum Technique," Miller et al., submitted to Transactions of the American Nuclear Society, Jan. 12, 1996, the content of which is hereby incorporated by reference.

The present invention relates to the device or "camera" that carries out the notched neutron spectrum technique to determine the hydrogen content of an irradiated BWR fuel element such as a fuel rod of a nuclear fuel bundle.

Figure 1:
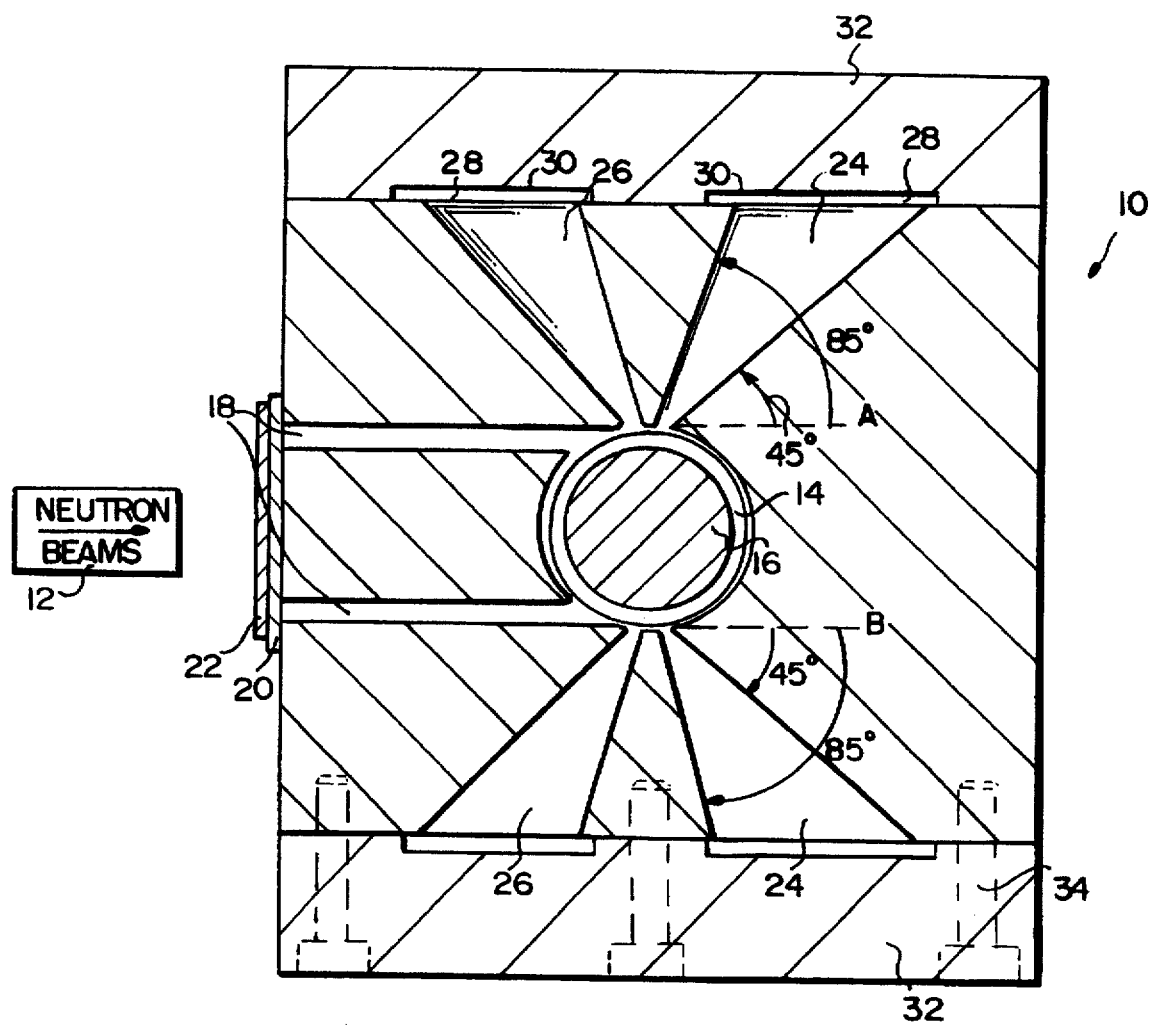
FIG. 1 is a horizontal cross-sectional view of the radiography camera according to the present invention.
Figure 2:
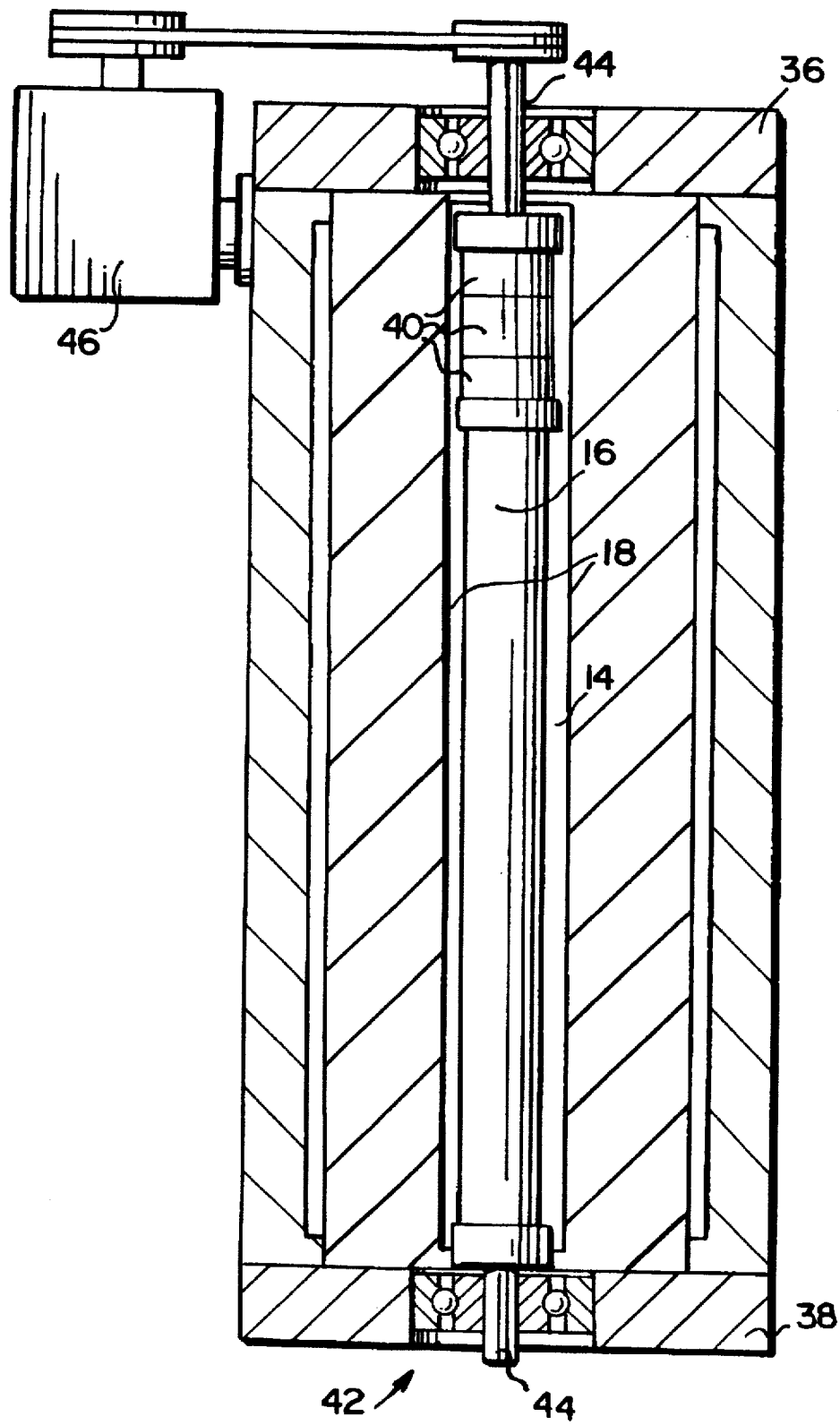
FIG. 2 is a vertical cross-sectional view of the radiography camera according to the present invention.

FIG. 1 is a horizontal cross-sectional view of the device according to the present invention. The "camera" according to the invention includes a base unit 10 that serves as a main support body for the elements of the camera. The base unit 10 is preferably formed of a material that shields the fuel element from the incident neutron beam. The camera operates in cooperation with a neutron beam source 12 disposed adjacent the base unit 10. The base unit 10 includes a central elongated channel 14 that is shaped to receive a BWR fuel element such as a zirconium clad nuclear fuel rod 16. As shown in FIG. 2, the central elongated channel 14 extends substantially along the entire length of the camera.

Extending substantially radially from the central elongated channel 14 are a plurality of input ports and scatter cavities. The base unit 10 preferably includes two substantially parallel incident neutron beam ports 18 that are aligned with the neutron beam source 12. The incident neutron beam ports 18 are preferably substantially parallel in the base unit 10 and are tangentially aligned with the central elongated channel 14. In this manner, the neutron beam is aimed directly at the periphery of the fuel rod at the location of the zirconium cladding. As a result, any remaining fuel in the fuel rod need not be removed.

The indium notched energy filter 20 and the cadmium thermal neutron filter 22 noted above are disposed covering the incident neutron beam ports 18 between the central elongated channel 14 and the neutron beam source 12. The indium notched energy filter 20 removes neutrons (by absorption) of specific energies from the incident neutron beam, and the cadmium thermal neutron filter 22 removes neutrons (by absorption) of thermal energy from the incident neutron beam. The amount of filtering and the manner in which the filters 20, 22 provide the desired notched neutron spectrum is known, and further description thereof will be omitted.

As noted above, collision of the neutrons with hydrogen in the zirconium cladding lowers the neutron energy and scatters the neutrons at preferential angles. As shown in FIG. 1, scatter cavities 24, 26 are formed in the base unit 10 in accordance with a scattered neutron path based on these preferential angles. A forward scatter cavity 24 and a back scatter cavity 26 are provided for each of the two incident neutron beam ports 18. Each scatter cavity 24, 26 is formed in the base unit 10 between predetermined angles from the central elongated channel 14 relative to an incident angle of the neutron beam. In particular, measuring in a counter clockwise direction from neutron beam A in FIG. 1, the forward scatter cavity 24 extends from the central elongated channel 14 between about a 45° angle to an 85° angle, and the back scatter cavity 26 extends between about a 95° angle and a 135° angle. The scatter cavities 24, 26 measured clockwise from neutron beam B are formed between similar predetermined angles. Thus, each scatter cavity 24, 26 encompasses about a 40° angle.

Absorber plates 28, such as indium foil, are disposed in resonance absorber cavities 30 at terminal ends of each of the scatter cavities 24, 26. The absorber plates 28 become activated by resonance absorption from the neutrons scattered by hydrogen in the target fuel elements.

The central elongated channel 14 is preferably drilled out of the base unit 10, and the beam ports 18 and cavities 24, 26 are preferably milled from the base unit. End caps 32 are secured by bolts 34 or the like to hold the base unit 10 together and enclose the camera along its longitudinal direction. The resonance absorber cavities 30 are formed in the end caps 32, and removal of the end caps 32 provide access to the resonance absorber cavities 30 and the absorber plates 28. Referring to FIG. 2, a top cap 36 and a bottom cap 38 enclose the base unit 10.

With continued reference to FIG. 2, the camera may optionally be provided with calibration sources 40 of known hydrogen content with the target fuel rods. The calibration sources 40 enable the entire process to be insensitive to variables such as exposure time and neutron beam intensity.

The BWR fuel element such as the fuel rod 16 may be rotatably supported in the central elongated channel 14 by a support assembly 42. The support assembly 42 includes a pair of bearing units 44 secured to the base unit 10 that facilitate rotation of the BWR fuel element 16. A motor 46 may be connected to the support assembly to rotatably drive the support assembly about a central longitudinal axis through the elongated central channel 14. With the support assembly 42 and drive motor 46, the fuel element can be rotated during neutron exposure to allow exposure of the entire zirconium cladding while minimizing exposure to the enclosed fuel pellet. Typically, the drive motor 46 rotates the fuel element at about 2 to 3 rpms.

The present invention provides a neutron radiography camera that carries out a method of determining hydrogen content in irradiated BWR fuel elements using a notched neutron spectrum. The non-destructive process enables post-hydrogen determination analysis of mechanical properties, enabling the coordination of hydride levels with mechanical properties. Moreover, because the camera according to the invention is portable, on-site measurements can be obtained.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A neutron radiography camera operating in cooperation with a neutron beam source for determining hydrogen content of irradiated BWR fuel elements, the camera comprising:

a base unit including a central elongated channel shaped to receive a BWR fuel element;

an incident neutron beam port formed in said base unit, said incident neutron beam port being tangentially aligned with said central elongated channel;

a filter assembly disposed between the neutron beam source and said incident neutron beam port, said filter assembly selectively filtering the neutron beam to remove certain energy levels; and an absorber plate disposed in a scattered neutron path.

2. A neutron radiography camera according to claim 1, wherein said filter assembly comprises a cadmium thermal neutron filter and an indium notched energy filter.

3. A neutron radiography camera according to claim 1, further comprising a scatter cavity formed in said base unit along said scattered neutron path, said scatter cavity being formed between predetermined angles from said central elongated channel relative to an incident angle of the neutron beam.

4. A neutron radiography camera according to claim 3, wherein said absorber plate is disposed at a terminal end of said scatter cavity.

5. A neutron radiography camera according to claim 3, comprising at least one forward scatter cavity formed in said base unit along a forward scattered neutron path, said forward scatter cavity being formed between predetermined obtuse angles from said central elongated channel relative to the incident angle of the neutron beam.

6. A neutron radiography camera according to claim 5, comprising at least one back scatter cavity formed in said base unit along a back scattered neutron path, said back scatter cavity being formed between predetermined acute angles from said central elongated channel relative to the incident angle of the neutron beam.

7. A neutron radiography camera according to claim 6, comprising at least two absorber plates, said absorber plates being disposed at terminal ends of said forward scatter cavity and said back scatter cavity, respectively.

8. A neutron radiography camera according to claim 7, wherein said absorber plates comprise indium foil.

9. A neutron radiography camera according to claim 7, comprising two incident neutron beam ports formed in said base unit.

10. A neutron radiography camera according to claim 9, comprising a forward scatter cavity and a back scatter cavity for each of said two incident neutron beam ports.

11. A neutron radiography camera according to claim 1, comprising two incident neutron beam ports formed in said base unit.

12. A neutron radiography camera according to claim 1, further comprising a support assembly rotatably disposed at opposite ends of said central elongated channel, said support assembly adapted to rotatably support the BWR fuel element in said central elongated channel.

13. A neutron radiography camera according to claim 12, wherein said support assembly comprises a pair of bearing units secured to said base unit, said bearing units facilitating rotation of the BWR fuel element.

14. A neutron radiography camera according to claim 13, further comprising a motor connected to said support assembly, said motor rotatably driving said support assembly about a central longitudinal axis through said central elongated channel.

15. A neutron radiography camera for determining hydrogen content of irradiated BWR fuel elements, the camera comprising:

a base unit including a central elongated channel shaped to receive a BWR fuel element;

an incident neutron beam port formed in said base unit, said incident neutron beam port being tangentially aligned with said central elongated channel and receiving an incident filtered neutron beam; and a scatter cavity formed in said base unit, said scatter cavity receiving neutrons scattered from hydrogen in the BWR fuel element.

16. A neutron radiography camera according to claim 15, further comprising a filter assembly disposed covering said incident neutron beam port, said filter assembly filtering a neutron beam from a neutron beam source.

17. A neutron radiography camera according to claim 16, wherein said filter assembly comprises a cadmium thermal neutron filter and an indium notched energy filter.

18. A neutron radiography camera according to claim 15, further comprising an absorber plate attached to said base unit at a terminal end of said scatter cavity.

19. A neutron radiography camera according to claim 18, wherein said absorber plate comprises indium foil.

20. A neutron radiography camera according to claim 15, comprising a plurality of scatter cavities, said scatter cavities being formed in said base unit between predetermined angles relative to an incident angle of said incident filtered neutron beam in accordance with a preferential path of scattered neutrons.

21. A neutron radiography camera according to claim 20, wherein said predetermined angles are about 45° and 85°.

* * * * *